United States Patent [19]

Brem et al.

[11] Patent Number: 5,626,862

[45] Date of Patent: May 6, 1997

[54] CONTROLLED LOCAL DELIVERY OF CHEMOTHERAPEUTIC AGENTS FOR TREATING SOLID TUMORS

[75] Inventors: Henry Brem, Lutherville, Md.; Robert S. Langer, Newton, Mass.; Abraham J. Domb, Efrat, Israel

[73] Assignees: Massachusetts Institute of Technology, Cambridge, Mass.; The Johns Hopkins University, Baltimore, Md.

[21] Appl. No.: 284,341

[22] Filed: Aug. 2, 1994

[51] Int. Cl.$^6$ .................................................. A61K 31/335
[52] U.S. Cl. ........................ 424/426; 424/1.11; 424/425
[58] Field of Search .............................. 424/486, 422, 424/484, 426, 485, 487, 488

[56] References Cited

U.S. PATENT DOCUMENTS

| | | | |
|---|---|---|---|
| 4,757,128 | 7/1988 | Domb et al. | 528/271 |
| 4,789,724 | 12/1988 | Domb et al. | 528/176 |
| 4,857,311 | 8/1989 | Domb et al. | 424/78 |
| 4,867,978 | 9/1989 | Gold | 424/719 |
| 4,888,176 | 12/1989 | Langer et al. | 424/426 |
| 4,943,579 | 7/1990 | Vishnuvajjala et al. | 514/283 |
| 5,064,823 | 11/1991 | Lee et al. | 514/198 |
| 5,145,684 | 9/1992 | Liversidge et al. | 424/489 |
| 5,225,404 | 7/1993 | Giovannella et al. | 514/81 |
| 5,362,831 | 11/1994 | Mongelli et al. | 526/304 |
| 5,380,751 | 1/1995 | Chen et al. | 514/449 |
| 5,395,850 | 3/1995 | Roth | 514/471 |

OTHER PUBLICATIONS

Walter et al., *Chem. Abs.* 120(22), 280088 (May 30, 1994).
Kaetsu et al.,*Chem. Abs.* 108(22) 192636 (May 30, 1988).
Straw et al., *Chem. Abs.* 121(20), 238234 (Nov. 14, 1994).
Auerbach et al., *Chem. Abs.* 121(1), 159 (Jul. 4, 1994).
Alkan–Onyuksel, Hayat, et al., "A Mixed Micellar Formulation Suitable for the Parenteral Administration of Taxol," *Pharm. Res.* 11(2):206–212 (1994).

Beckman, G., et al., "G–6–PD and PGM Phenotypes of 16 Continuous Human Tumor Cell Lines," *Hum. Hered.* 21:238–241 (1971).

Brem, Henry, et al., "Polymers as Controlled Drug Delivery Devices for the Treatment of Malignant Brain Tumors," *Eur. J. Pharm. Biopharm.* 39(1):2–7 (1993).

Brem, Henry, et al., "Interstitial chemotherapy with drug polymer implants for the treatment of recurrent gliomas," *J. Neurosurg.* 74:441–446 (1991).

Brem, Henry, et al., "Intraoperative Chemotherapy using biodegradable polymers: Safety and Effectiveness for Recurrent Glioma Evaluated by a Prospective, Multi–Institutional Placebo–Controlled Clinical Trail," *Proc. Amer. Soc. Clin. Oncology* May 17, 1994.

(List continued on next page.)

*Primary Examiner*—Thurman K. Page
*Assistant Examiner*—Sharon Howard
*Attorney, Agent, or Firm*—Arnall Golden & Gregory

[57] ABSTRACT

A method and devices for localized delivery of a chemotherapeutic agent to solid tumors, wherein the agent does not cross the blood-brain barrier and is characterized by poor bioavailability and/or short half-lives in vivo, are described. The devices consist of reservoirs which release drug over an extended time period while at the same time preserving the bioactivity and bioavailability of the agent. In the most preferred embodiment, the device consists of biodegradable polymeric matrixes, although reservoirs can also be formulated from non-biodegradable polymers or reservoirs connected to implanted infusion pumps. The devices are implanted within or immediately adjacent the tumors to be treated or the site where they have been surgically removed. The examples demonstrate the efficacy of paclitaxel and camptothecin delivered in polymeric implants prepared by compression molding of biodegradable and non-biodegradable polymers, respectively. The results are highly statistically significant.

18 Claims, 3 Drawing Sheets

OTHER PUBLICATIONS

Bullard, Dennis E., et al., "Growth and Chemotherapeutic Response in Athymic Mice of Tumors Arising from Human Glioma–derived Cell Lines," *J. Neuropathol. Exp. Neurol.* 40:410–427 (1981).

Domb, A.J. and R. Langer, "Polyanhydrides. I. Preparation of High Molecular Weight Polyanhydrides," *J. Polym. Sci.* 25:3373–3386 (1987).

Domb, et al., "In Vitro Release Kinetics Studies," *Polym. Prepr.* 32(2):219–220 (1991).

Gottlieb, Jeffrey A., and James K. Luce, "Treatment of Malignant Melanoma With Camptothecin (NSC–100880)," *Cancer Chemother. Rep.* 56(1):103–105 (1972).

Gottlieb, Jeffrey A., et al., "Preliminary Pharmacologic and Clinical Evaluation of Camptothecin Sodium (NSC–100880)," *Cancer Chemother. Rep.* 54(6):461–470 (1970).

Grossman, Stuart, et al., "The intracerebral distribution of BCNU delivered by surgically implanted biodegradable polymers," *J. Neurosurg.* 76:640–647 (1992).

Hanauske, Axel–R., et al., "Effects of Taxotere and taxol on in vitro colony formation of freshly explanted human tumor cells," *Anticancer Drugs* 3:121–124 (1992).

*Harrison's Principles of Internal Medicine* 431–446, E. Braunwald et al., ed., McGraw–Hill Book Co. (1987).

Horwitz, S.B., et al., "Taxol: Mechanisms of Action and Resistance," *Ann. NY Acad. Sci.* 466:733–744 (1986).

Jacobsen, P.F., et al., "Establishment of a Human Medulloblastoma Cell Line and Its Heterotransplantation into Nude Mice," *J. Neuropathol. Exp. Neurol.* 44:472–485 (1985).

Jampel, Henry D., and Paroo Koya, "In Vitro Release of Hydrophobic Drugs From Polyanhydride Disks," *Opthalmic Surg.* 22.676–680 (1991).

Klecker, R.W., et al., "Distribution and metabolism of $^3$H–taxol in the rat," *Proc. Am. Assoc. Cancer Res.* 43:380 (1993).

Langer, Robert and Judah Folkman, "Polymers for the sustained release of proteins and other macromolecules," *Nature (London)* 263:797–799 (1976).

Langer, Robert, et al., "Biocompatibility of polymeric delivery systems for macromolecules," *J. Biomed. Mater. Res.* 15:267–277 (1981).

Leong, K.W., et al., "Bioerodible polyanhydrides as drug–carrier matrices. I: Characterization, degradation, and release characteristics," *J. Med. Biomed. Mater. Res.* 19:941 (1985).

Leong, K.W., et al. "Bioerodible polyanhydrides as drug–carrier matrices. II. Biocompatibility and chemical reactivity," *J. Med. Biomed. Mater. Res.* 20:51 (1986).

Moertel, Charles G., et al., "Phase II Study of Camptothecin (NSC–100880) in the Treatment of Advanced Gastrointestinal Cancer," *Cancer Chemother. Rep.* 56(1):95–101 (1972).

Muggia, Franco M., et al., "Phase I Clinical Trial Weekly and Daily Treatment with Camptothecin (NSC–100880): Correlation with Preclinical Studies," *Cancer Chemother. Rep.* 56(4):515–521 (1972).

Rhine, William D., et al., "Polymers for Sustained Macromolecule Release: Procedures to Fabricate Reproducible Delivery Systems and Control Release Kinetics," *J. Pharm. Sci.* 69:265–270 (1980).

Ringel, Israel, and Susan Band Horwitz, "Taxol is Converted to 7–Epitaxol, a Biologically Active Isomer, in Cell Culture Medium," *J. Pharmacol. Exp. Ther.* 242:692–698 (1987).

Rosen, H.B., et al., "Bioerodible polyanhydrides for controlled drug delivery," *Biomaterials* 4:131 (1983).

Rosenblum, Mark L., et al., "Development of a Clonogenic Cell Assay for Human Brain Tumors," *Cancer* 41:2305–2314 (1978).

Roth, B., et al., "Taxol (NSC 125973) in Advanced, Hormone–Refractory Prostate Cancer: An Ecog Phase II Trail," *Pr. Annu. Meet. Am. Soc. Clin. Oncol.* 11:A598 (1992).

Rowinsky, Eric K., et al., "Microtubule Chanes and Cytotoxicity in Leukemic Cell Lines Treated with Taxol," *Cancer Res.* 48:4093–4100 (1988).

Rowinsky, Eric K., et al., "Phase I and Pharmacodynamic Study of Taxol in Refractory Acute Leukemias," *Cancer Res.* 49:4640–4647 (1989).

Rowinsky, Eric K., et al., "Taxol: A Novel Investigational Antimicrotubule Agent," *J. Natl. Cancer Inst.* 82:1247–1259 (1990).

Roytta, Matias, et al., "Morphological Studies on the Effect of Taxol on Cultured Human Prostatic Cancer Cells," *Prostate* 11:95–106 (1987).

Salcman, Michael, et al., "In Vitro Response of Human Glioblastoma and Canine Glioma Cells to Hyperthermia, Radiation, and Chemotherapy," *Neurosurgery* 29:526–531 (1991).

Sarosy, Gisele and Eddie Reed, "Taxol Dose Intensification and Its Clinical Implications," *J. Nat. Med. Assoc.* 85(6):427–431 (1993).

Slichenmyer, William J., et al., "New Natural Products in Cancer Chemotherapy," *J. Clin. Pharmacol.* 30:770–788 (1990).

Tamargo, Rafael J., et al. "Interstitial Chemotherapy of the 9L Gliosarcoma: Controlled Release Polymers for Drug Delivery in the Brain," *Cancer Res.* 53:329–333 (1993).

Tamita, T., "Interstitial chemotherapy for brain tumors: review" *J. Neuro–Oncology* 10:57–74 (1991).

Venditti, John M., and Betty J. Abbott, "Studies on Oncolytic Agents from Natural Sources, Correlations of Activity Against Animal Tumors and Clinical Effectiveness," *Lloydia* 30:332–348 (1967).

CONTROLLED LOCAL DELIVERY OF CHEMOTHERAPEUTIC AGENTS FOR TREATING SOLID TUMORS

The U.S. government has rights in this invention by virtue of a grant from the National Cancer Institute, cooperative agreement number U01 CA 52857; and N.I.H. grant numbers U01 CA52857 to Henry Brem and Robert S. Langer and T32 CA09574.

BACKGROUND OF THE INVENTION

This invention is in the field of localized delivery of chemotherapeutic agents to solid tumors.

One-third of all individuals in the U.S. alone will develop cancer. Although the five-year survival rate has risen dramatically to nearly fifty percent as a result of progress in early diagnosis and the therapy, cancer still remains second only to cardiac disease as a cause of death in the U.S. Twenty percent of Americans die from cancer, half due to lung, breast, and colon-rectal cancer.

Designing effective treatments for patients with cancer has represented a major challenge. The current regimen of surgical resection, external beam radiation therapy, and/or systemic chemotherapy has been partially successful in some kinds of malignancies, but has not produced satisfactory results in others. In some malignancies, such as brain malignancies, this regimen produces a median survival of less than one year. For example, 90% of resected malignant gliomas recur within two centimeters of the original tumor site within one year.

Though effective in some kinds of cancers, the use of systemic chemotherapy has had minor success in the treatment of cancer of the colon-rectum, esophagus, liver, pancreas, and kidney and melanoma. A major problem with systemic chemotherapy for the treatment of these types of cancer is that the systemic doses required to achieve control of tumor growth frequently result in unacceptable systemic toxicity. Efforts to improve delivery of chemotherapeutic agents to the tumor site have resulted in advances in organ-directed chemotherapy, as by continuous systemic infusion, for example. However, continuous infusions of anticancer drugs generally have not shown a clear benefit over pulse or short-term infusions. Implantable elastomer access ports with self-sealing silicone diaphragms have also been tried for continuous infusion, but extravasation remains a problem. Portable infusion pumps are now available as delivery devices and are being evaluated for efficacy. (See *Harrison's Principles of Internal Medicine* 431–446, E. Braunwald et al., ed., McGraw-Hill Book Co. (1987) for a general review).

In the brain, the design and development of effective anti-tumor agents for treatment of patients with malignant neoplasms of the central nervous system have been influenced by two major factors: 1) the blood-brain barrier provides an anatomic obstruction, limiting access of drugs to these tumors; and 2) the drugs given at high systemic levels are generally cytotoxic. Efforts to improve drug delivery to the tumor bed in the brain have included transient osmotic disruption of the blood brain barrier, cerebrospinal fluid perfusion, and direct infusion into a brain tumor using catheters. Each technique has had significant limitations. Disruption of the blood brain barrier increased the uptake of hydrophilic substances into normal brain, but did not significantly increase substance transfer into the tumor. Only small fractions of agents administered into the cerebrospinal fluid actually penetrated into the brain parenchyma. Drugs that have been used to treat tumors by infusion have been inadequate, did not diffuse an adequate distance from the site of infusion, or could not be maintained at sufficient concentration to allow a sustained diffusion gradient. The use of catheters has been complicated by high rates of infection, obstruction, and malfunction due to clogging. See T. Tomita, "Interstitial chemotherapy for brain tumors: review" *J. Neuro-Oncology* 10:57–74 (1991).

Controlled release biocompatible polymers for local drug delivery have been utilized for contraception, insulin therapy, glaucoma treatment, asthma therapy, prevention of dental caries, and certain types of cancer chemotherapy. (Langer, R., and D. Wise, eds, *Medical Applications of Controlled Release*, Vol. I and II, Boca Raton, CRC Press (1986)) Brain tumors have been particularly refractory to chemotherapy. One of the chief reasons is the restriction imposed by the blood-brain barrier. Agents that appear active against certain brain tumors, such as gliomas, in vitro may fail clinical trials because insufficient drug penetrates the tumor. Although the blood-brain barrier is disrupted at the core of a tumor, it is largely intact at the periphery where cells actively engaged in invasion are located. Experimental intratumoral regimens include infusing or implanting therapeutic agents within the tumor bed following surgical resection, as described by Tamita, T, *J. Neuro-Oncol.* 10:57–74 (1991).

Delivery of a low molecular weight, lipid soluble chemotherapeutic, 1,3-bis(2-chloroethyl)-1-nitrosourea (BCNU), in a polymer matrix implanted directly adjacent to brain tumors has some efficacy, as reported by Brem, et al., *J. Neurosurg.* 74:441–446 (1991); Brem, et al., *Eur. J. Pharm. Biopharm.* 39(1):2–7 (1993); and Brem, et al., "Intraoperative Chemotherapy using biodegradable polymers: Safety and Effectiveness for Recurrent Glioma Evaluated by a Prospective, Multi-Institutional Placebo-Controlled Clinical Trial" *Proc. Amer. Soc. Clin. Oncology* May 17, 1994. Polymer-mediated delivery of BCNU was superior to systemic delivery in extending survival of animals with intracranial 9L gliosarcoma and has shown some efficacious results in clinical trials. However, BCNU is a low molecular weight drug, crosses the blood-barrier and had previously been demonstrated to have some efficacy when administered systemically.

Unfortunately, the predictability of the efficacy of chemotherapeutic agents remains low. Drugs that look effective when administered systemically to animals may not be effective when administered systemically to humans due to physiological differences and bioavailability problems, and drugs that are effective systemically may not be effective when administered locally.

For example, one promising chemotherapeutic, camptothecin, a naturally occurring alkaloid isolate from *Camptotheca acuminata*, a tree indigenous to China, which exerts its pharmacological effects by irreversibly inhibiting topoisomerase I, an enzyme intimately involved in DNA replication, has been shown to have strong cytotoxic anti-tumor activity against a variety of experimental tumors in vitro, such as the L1210 and rat Walker 256 carcinosarcoma (Venditti, J. M., and B. J. Abbott, *Lloydia* 30:332–348 (1967); Moertel, C. G., et al., *Cancer Chemother. Rep.* 56(1):95–101 (1972)). Phase I and II clinical trials of camptothecin in human patients with melanoma and advanced gastrointestinal carcinoma, however, have shown unexpectedly severe systemic toxicity with poor tumoral responses, and clinical investigation therefore halted. (Gottlieb, J. A., and J. K. Luce, *Cancer Chemother. Rep.* 56(1):103–105 (1972); Moertel, C. G., et al., *Cancer Chemother. Rep.* 56(1):95–101 (1972); Muggia, F. M., et al., *Cancer Chemother. Rep.* 56(4):515–521 (1972)). Further pharmacological evaluation by Gottlieb, et al., *Cancer Chemother. Rep.* 54(6):461–470 (1970) and Slichenmyer, et al., *J. Clin. Pharmacol.* 30:770–788 (1990), revealed that the sodium salt formulation of camptothecin was strongly protein-bound and required conversion to a lactone structure for activity. The alkaloid, a 4-ethyl-4-hydroxy-1H- pyrano-[3',4':6,7]indolizino[1,2-b] quinoline-3,14(4H,12H)-dione, having a molecular weight of 348, is not only water insoluble, but even crystallizes out of acetonitrile-methanol, and does not form stable salts with acids. The poor bioavailability may explain the lack of in vivo efficacy.

Many other chemotherapeutics which are efficacious when administered systemically must be delivered at very high dosages in order to avoid toxicity due to poor bioavailability. For example, paclitaxel (taxol) has been used systemically with efficacy in treating several human tumors, including ovarian, breast, and non-small cell lung cancer. However, maintenance of sufficient systemic levels of the drug for treatment of tumors has been associated with severe, in some cases "life-threatening" toxicity, as reported by Sarosy and Reed, J. Nat. Med. Assoc. 85(6):427–431 (1993). Paclitaxel is a high molecular weight (854), highly lipophilic deterpenoid isolated from the western yew, Taxus brevifolia, which is insoluble in water. It is normally administered intravenously by dilution into saline of the drug dissolved or suspended in polyoxyethylated castor oil. This carrier has been reported to induce an anaphylactic reaction in a number of patients (Sarosy and Reed (1993)) so alternative carriers have been proposed, such as a mixed micellar formulation for parenteral administration, described by Alkan-Onyuksel, et al., Pharm. Res. 11(2), 206–212 (1994). There is also extensive non-renal clearance, with indications that the drug is removed and stored peripherally. Pharmacokinetic evidence from clinical trials (Rowinsky, E. K., et al., Cancer Res. 49:4640–4647 (1989)) and animal studies (Klecker, R. W., Proc. Am. Assoc. Cancer Res. 43:381 (1993)) indicates that paclitaxel penetrates the intact blood-brain barrier poorly, if at all, and that there is no increased survival from systemic intraperitoneal injections of paclitaxel into rats with intracranial gliomas. Paclitaxel has been administered in a polymeric matrix for inhibition of scar formation in the eye, as reported by Jampel, et al., Opthalmic Surg. 22, 676–680 (1991), but has not been administered locally to inhibit tumor growth.

It is therefore an object of the present invention to provide a chemotherapeutic composition and method of use thereof which provides for effective long term release of chemotherapeutic agents that are not stable or soluble in aqueous solutions or which have limited bioavailability in vivo for treatment of solid tumors.

It is a further object of the present invention to provide a composition and method of use for the treatment of solid tumors with chemotherapeutic agents that avoids high systemic levels of the agent and associated toxicities.

SUMMARY OF THE INVENTION

A method and devices for localized delivery of a chemotherapeutic agent to solid tumors, wherein the agent does not cross the blood-brain barrier and is characterized by poor bioavailability and/or short half-lives in vivo, are described. The devices consist of reservoirs which release drug over an extended time period while at the same time preserving the bioactivity and bioavailability of the agent. In the most preferred embodiment, the device consists of biodegradable polymeric matrixes, although reservoirs can also be formulated from non-biodegradable polymers or reservoirs connected to implanted infusion pumps. The devices are implanted within or immediately adjacent the tumors to be treated or the site where they have been surgically removed.

The examples demonstrate the efficacy of paclitaxel and camptothecin delivered in polymeric implants prepared by compression molding of biodegradable and non-biodegradable polymers, respectively, against a number of human tumor cell lines, both in vitro and in vivo. The results are highly statistically significant.

DETAILED DESCRIPTION OF THE INVENTION

One method of extending the duration of exposure of a tumor to a drug is to deliver the drug interstitially to the tumor. Controlled-infusion pumps and biodegradable polymer devices are currently being developed to deliver drugs in such a sustained fashion to tumors of the central nervous system. Interstitial delivery minimizes the systemic drug levels and side effects of an agent. Delivering chemotherapeutic drugs locally to a tumor is an effective method of prolonging tumor exposure to the drug while minimizing the drug's dose-limiting systemic side effects, such as neutropenia.

Interstitial drug delivery also bypasses the limitations of the blood-brain barrier. Presently, it is unclear how well some drugs such as paclitaxel crosses the blood-brain barrier.

As described herein, a composition is formulated of a chemotherapeutic agent which is not water soluble and has poor bioavailability in vivo encapsulated into a biocompatible polymeric matrix, most preferably biodegradable, for use in treatment of solid tumors. The agent is released by diffusion and/or degradation over a therapeutically effective time, usually eight hours to five years, preferably one week to one year.

Polymeric Formulations

The ideal polymeric matrix would combine the characteristics of hydrophobicity, stability, organic solubility, low melting point, and suitable degradation profile. The polymer must be hydrophobic so that it retains its integrity for a suitable period of time when placed in an aqueous environment, such as the body, and be stable enough to be stored for an extended period before use. The ideal polymer must also be strong, yet flexible enough so that it does not crumble or fragment during use.

Biocompatible polymers can be categorized as biodegradable and non-biodegradable. Biodegradable polymers degrade in vivo as a function of chemical composition, method of manufacture, and implant structure. Synthetic and natural polymers can be used although synthetic polymers are preferred due to more uniform and reproducible degradation and other physical properties. Examples of synthetic polymers include polyanhydrides, polyhydroxyacids such as polylactic acid, polyglycolic acids and copolymers thereof, polyesters, polyamides, polyorthoesters, and some polyphosphazenes. Examples of naturally occurring polymers include proteins and polysaccharides such as collagen, hyaluronic acid, albumin and gelatin. Drug can be encapsulated within, throughout, and/or on the surface of the implant. Drug is released by diffusion, degradation of the polymer, or a combination thereof. There are two general classes of biodegradable polymers: those degrading by bulk erosion and those degrading by surface erosion. The latter polymers are preferred where more linear release is required. The time of release can be manipulated by altering chemical composition; for example, by increasing the amount of an aromatic monomer such as p-carboxyphenoxy propane (CPP) which is copolymerized with a monomer such as sebacic acid (SA). A particularly preferred polymer is CPP-SA (20:80).

Use of polyanhydrides in controlled delivery devices has been reported by Leong, et al., *J. Med. Biomed. Mater. Res.* 19, 941 (1985); *J. Med. Biomed. Mater. Res.* 20, 51 (1986); and Rosen, et al., *Biomaterials* 4, 131 (1983). The release and physical properties required for processing into implants are largely determined by the hydrophobicity and molecular weight, with higher molecular weight polymers having more desirable physical properties. Aromatic polyanhydrides exhibit near zero order (linear) erosion and release kinetics, but have very slow degradation rates. For example, it was estimated that it would take a delivery device prepared from p-CPP more than three years to completely degrade in vivo. Polymers prepared from linear aliphatic diacids are hydrophilic solids that degrade by bulk erosion, resulting in a rapid release of the drug from the polymeric matrix. Further, anhydride homopolymers based on aromatic or linear aliphatic dicarboxylic acids are highly crystalline and have poor film forming properties. Aromatic polyanhydrides also have high melting points and low solubility in organic solvents. Copolymerizing the linear aliphatic diacids with aromatic diacids, to form, for example, the copolymer of poly 1,3-(bis(p-carbophenoxy)propane anhydride (p-CPP) (an aromatic polyanhydride) with sebacic acid (a copolymer of an aromatic diacid and an aliphatic diacid), can be used to obtain polymers having appropriate degradation times. As described in U.S. Pat. No. 4,757,128 to Domb and Langer, high molecular weight copolymers of aliphatic dicarboxylic acids with aromatic diacids are less crystalline than aromatic or linear aliphatic polyanhydrides, and they form flexible films. U.S. Patents that describe the use of polyanhydrides for controlled delivery of substances include U.S. Pat. Nos. 4,857,311 to Domb and Langer, 4,888,176 to Langer, et al., and 4,789,724 to Domb and Langer.

Other polymers such as polylactic acid, polyglycolic acid, and copolymers thereof have been commercially available as suture materials for a number of years and can be readily formed into devices for drug delivery.

Non-biodegradable polymers remain intact in vivo for extended periods of time (years). Drug loaded into the non-biodegradable polymer matrix is released by diffusion through the polymer's micropore lattice in a sustained and predictable fashion, which can be tailored to provide a rapid or a slower release rate by altering the percent drug loading, porosity of the matrix, and implant structure. Ethylene-vinyl acetate copolymer (EVAc) is an example of a nonbiodegradable polymer that has been used as a local delivery system for proteins and other macromolecules, as reported by Langer, R., and J. Folkman, *Nature (London)* 263:797–799 (1976). Others include polyurethanes, polyacrylonitriles, and some polyphosphazenes.

Compounds to be Encapsulated

Chemotherapeutic Agents

A variety of different chemotherapeutic agents can be incorporated into the polymeric matrix. In general, drugs will be added to between 10 and 50% (w/w), although the optimum can vary widely depending on the drug, from 1% to 90%.

Table 1 is a summary of studies on intracranial local drug delivery in rat glioma models, as described in the following examples.

TABLE 1

Summary of intracranial local drug delivery.
Median survival in days

| Drug | Tumor | polymer | $R_x$ day | controls (n) | $R_x$ group (n) | % increase survival | p value |
| --- | --- | --- | --- | --- | --- | --- | --- |
| campto-thecin | 9L ($2 \times 2 \times 1$ mm$^3$) | EVAc (50% load) | 5 | 19 | >120 | >530% | <0.001 |
| | 9L ($2 \times 2 \times 1$ mm$^3$) | p(CPP:SA) (50% load) | 5 | 24 (n = 10) | 43 (n = 10) | 79% | N.A. |
| BCNU | 9L ($2 \times 2 \times 1$ mm$^3$) | EVAc (30% load) | 4 | 10.9 (n = 12) | 80 (n = 12) | 634% | <0.05 |
| | 9L ($2 \times 2 \times 1$ mm$^3$) | p(CPP:SA) (30% load) | 4 | 11.6 (n = 12) | 62.3 (n = 12) | 437% | <0.05 |
| 4-HC | 9L ($1 \times 1 \times 1$ mm$^3$) | p(FAD:SA) (20% load) | 3 | 14 (n = 10) | 77 (n = 10) | 450% | <0.005 |
| | 9L ($1 \times 1 \times 1$ mm$^3$) | p(CPP:SA) (20% load) | 5 | 14 (n = 8) | 44.5 (n = 8) | 218% | |
| minocy-cline | 9L ($1 \times 1 \times 1$ mm$^3$) | EVAc (50% load) | 0 | 13 (n = 10) | 69 (n = 10) | 430% | <0.001 |
| | 9L | EVAc | 5 | 13 | 13 | 0 | NS |

TABLE 1-continued

Summary of intracranial local drug delivery.
Median survival in days

| Drug | Tumor | polymer | $R_x$ day | controls (n) | $R_x$ group (n) | % increase survival | p value |
|---|---|---|---|---|---|---|---|
| | (1 × 1 × 1 mm³) 9L | (50% load) EVAc | 5 | (n = 17) — | (n = 8) — | 43% | <0.002 |
| | (1 × 1 × 1 mm³) 9L | (50% load) EVAc | (+rsxn) 5 | (n = 18) — | (n = 17) — | 93% >ip BCNU | <0.002 |
| | (1 × 1 × 1 mm³) | (50% load) | (+ipBCNU) | (n = 17) | (n = 23) | 330% >no Rx <0.001 | |
| Carbo-platin | F98 inj. (1 × 10⁵ cells) | p(FAD:SA) (5% load) | 5 | 16 (n = 18) | 52 (n = 18) | 225% | <0.001 |
| Taxol | 9L (1 × 1 × 1 mm³) | p(CPP:SA) (20% load) | 5 | 19.5 (n = 8) | 61.5 (n = 8) | 215% | <0.001 |
| Methotrexate & dextran mix | 9L (2 × 2 × 1 mm³) | P(FAD:SA) (.01% load) | 5 | 18.6 (n = 8) | 23.0 (n = 8) | 60% | |

The preferred chemotherapeutic agents are camptothecin and paclitaxel, which are insoluble in water, relatively insoluble in lipid (compared, for example, to BCNU), high molecular weight (i.e., of a molecular weight not normally crossing the blood brain barrier), exhibit rapid non-renal clearance in vivo, and have substantial systemic toxicity, and their functionally effective derivatives. As used herein, paclitaxel refers to paclitaxel and functionally equivalent derivatives thereof, and camptothecin refers to camptothecin and functionally equivalent derivatives thereof.

Figure 1:
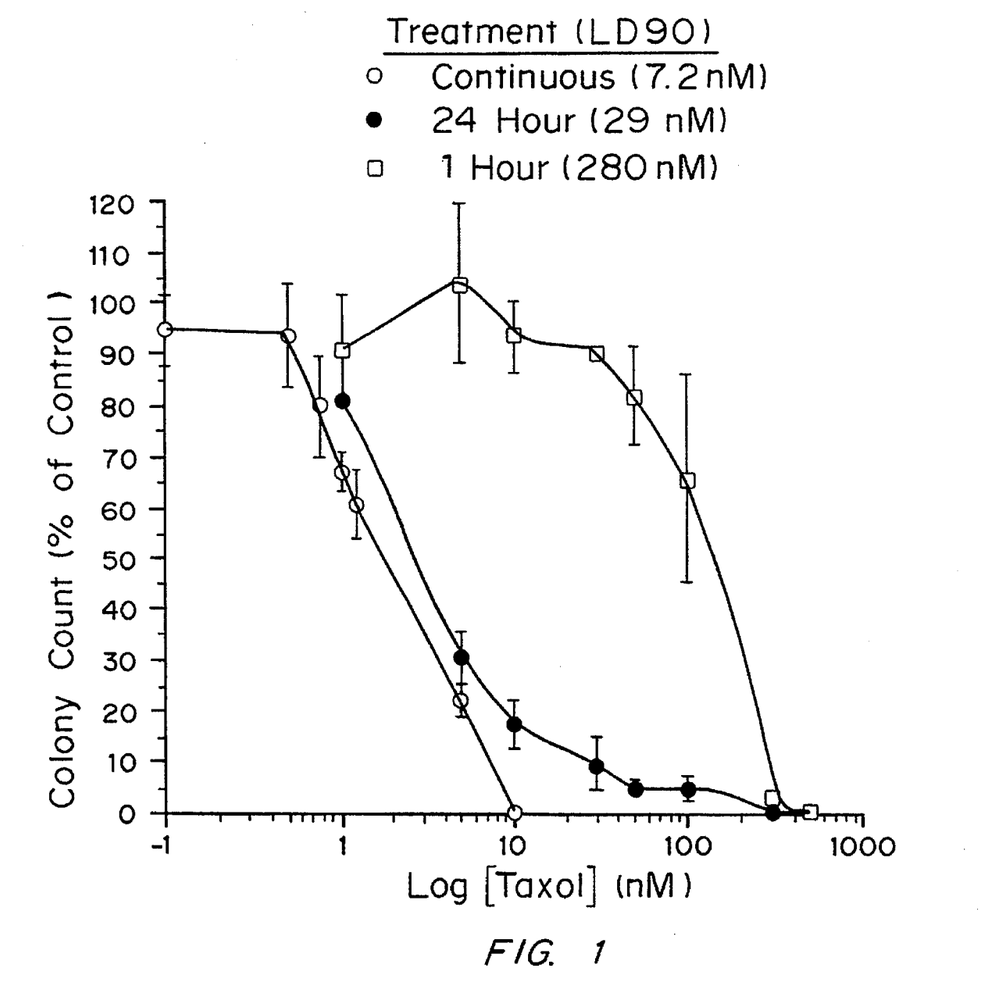
FIG. 1 is a graph showing paclitaxel cell kill as determined by a clonogenic assay versus the human glioma U373 cell line with 1-h ($LD_{90}$=280 nM, open squares), 24-h ($LD_{90}$=29 nM, dark circles), and continuous 6- to 8- day exposure ($LD_{90}$=7.2 nM, open circle) to the drug, shown as colony count (% of control) log concentration of paclitaxel in nM.

The preferred weight percent range of drug in polymer is from one to 90% and the preferred time of degradation is between one week and one year, for both paclitaxel and camptothecin. Dosages must be optimized depending on the size of the implant, the location and size of the tumor to be treated, and the period over which drug is to be delivered. These calculations are routine for those skilled in the art of administering chemotherapy to tumor patients. In general, the effective dosage of a chemotherapeutic agent which is administered locally by extended release will be significantly less than the dosage for the same drug administered for shorter periods of time. For example, as shown in FIG. 1, described in Example 1, and Table 3, the $LD_{90}$ for paclitaxel administered in a one hour infusion is 280 nM; for paclitaxel in a 24 hour infusion it is 29 nM; for continuous extended release it is 7.2 nM.

TABLE 2

In vitro efficacy of Camptothecin and
Paclitaxel on several cell lines.

| Camptothecin Cell line | Range $LD_{90}$ 1 h exposure (μM) | $LD_{90}$ continuous exposure (μM) |
|---|---|---|
| F98 | | |
| 9L | | |
| U87 | 0.1 to 1.40 | 0.026 to 0.10 |
| U373 | | |
| JH1 | | |
| Paclitaxel Cell line | Range $LD_{90}$ 1 h exposure (μM) | $LD_{90}$ continuous exposure (μM) |
| 9L | | |
| F98 | | |
| U373 | 0.280 to 0.890 | 0.0072 to 0.042 |
| H80 | | |
| U87 | | |
| D324 | | |

Adriamycin (doxorubicin) is another chemotherapeutic which can be utilized. Gliomas are highly sensitive to this drug in vitro, there is significant dose related cardiac toxicity, and there is synergy with tumor vaccines and immune based therapy. For incorporation into polymers, the drug is soluble in water, methanol, and aqueous alcohols. It is insoluble in acetone, benzene, chloroform, ethyl ether, and petroleum ether. An ideal release profile would have extended release over a period of at least one month. The dosage based on $LD_{90}$ for glioma lines ranges from 10 to 100 ng/ml.

Combinations with other biologically active
compounds

These chemotherapeutic agents can also be administered in combination with each other or other chemotherapeutic agents, including radiation therapy. Examples of other chemotherapeutic agents include cytotoxic agents such as ternozolamide, platinum drugs such as cisplatin, differentiating agents such as butyrate derivatives, transforming growth factor such as factor-alpha-Pseudomonas exotoxin fusion protein, and antibodies to tumor antigens, especially glioma antigens, such as monoclonal antibody 81C6.

Therapeutic immune responses can be modified by generation and enhancement of a systemic inflammatory response directed against a tumor and enhancement of a local inflammatory response to the tumor. Granulocyte-macrophage colony stimulating factor (GM-CSF) is an example of a cytokine systemically activating cytotoxic T lymphocytes (CTL) which has been shown to lead to the elimination of tumor cells in a potent and specific manner, by stimulating the growth and activity of several myeloid cells and playing a critical role in the migration and development of professional antigen present cells such as dendritic cells. Tumor specific CTL induction and systemic protection from tumor challenge can be generated by the subcutaneous injection of irradiated tumor cells genetically modified to produce the cytokine granulocyte-macrophage colony stimulating factor (GM-CSF). In one embodiment, killed tumor cells are transduced with the gene encoding GM-CSF and administered as a vaccine to stimulate CTL activation. This can be done prior to or in combination with implantation or local delivery of the chemotherapeutic agents. Other cytokines such as interleukin 2 (IL-2), tumor necrosis factor (TNF) and IL-4, as well as IL-5, IL-6 and gamma interferon (although not as well), act locally to stimulate tumor responses. IL-2 induces a local inflammatory response leading to activation of both helper and cytotoxic subsets of T cells. IL-4 has broad immunoregulatory properties. TNF-α has a diverse range of biological properties including generation of a number of cytokines such as IL-6, IL8, GM-CSF, and G-CSF, as well as the generation of hemorrhagic necrosis in established tumors. These are highly effective if administered in the polymeric matrix with the chemotherapeutic drug or in the form of transduced cells expressing IL-2 which are co-administered to the animal. Other vaccines and immunotoxins are also well known to those skilled in the art.

Examples of preferred combinations include combinations of cytotoxic agents or of cytotoxic agent and inhibitors 4-HC and topoisomerase inhibitors such as camptothecin, 4-HC and BCNU, BCNU and 06-BG, 4-HC and novobiocin, 4-HC and novobiocin, and 4-HC and BSO; combinations of cytoxic agents and other agents such as alkylating agents and differentiating agents (4HC and phenylbutyrate) and cytoxic agents and biologics (antibodies, immunotoxins, or growth factor linked toxins), and combinations of chemotherapeutic, cytokine (interleukin) and fumagillin. Other agents that can be incorporated include anti-angiogenesis agents and radiosensitizers, which are known to those skilled in the art. For example, paclitaxel is known to be effective as a radiosensitizer.

The same methods described with reference in the literature to incorporation of BCNU, and herein with reference to incorporation of camptothecin and paclitaxel, can be used to incorporate these compounds into polymeric matrices. See, for example, Domb, et al., Polym. Prepr. 32(2):219–220 (1991), reported incorporating the water soluble chemotherapeutic agents carboplatin, an analog of cisplatin, and 4-hydroperoxycyclophosphamide into a biodegradable polymer matrix for treating tumors, with promising results in animals.

In variations of these embodiments, it may be desirable to include other pharmaceutically active compounds, such as antiinflammatories or steroids which are used to reduce swelling, antibiotics, antivirals, or antibodies. For example, dexamethasone, a synthetic corticosteroid used systemically to control cerebral edema, has been incorporated into a non-biodegradable polymer matrix and tested in rat brain in vitro and in vivo for efficacy in reversing cerebral edema. Other compounds which can be included are preservatives, antioxidants, and fillers, coatings or bulking agents which may also be utilized to alter polymeric release rates.

Additives that are used to alter properties of the polymeric composition

In the preferred embodiment, only polymer and drugs to be released are incorporated into the delivery device, although other biocompatible, preferably biodegradable or metabolizable, materials can be included for processing purposes.

Buffers, acids and bases are used to adjust the pH of the composition. Agents to increase the diffusion distance of agents released from the implanted polymer can also be included.

Fillers are water soluble or insoluble materials incorporated into the formulation to add bulk. Types of fillers include sugars, starches and celluloses. The amount of filler in the formulation will typically be in the range of between about 1 and about 90% by weight.

Spheronization enhancers facilitate the production of spherical implants. Substances such as zein, microcrystalline cellulose or microcrystalline cellulose co-processed with sodium carboxymethyl cellulose confer plasticity to the formulation as well as implant strength and integrity. During spheronization, extrudates that are rigid, but not plastic, result in the formation of dumbbell shaped implants and/or a high proportion of fines. Extrudates that are plastic, but not rigid, tend to agglomerate and form excessively large implants. A balance between rigidity and plasticity must be maintained. The percent of spheronization enhancer in a formulation depends on the other excipient characteristics and is typically in the range of 10–90% (w/w).

Disintegrants are substances which, in the presence of liquid, promote the disruption of the implants. The function of the disintegrant is to counteract or neutralize the effect of any binding materials used in the formulation. The mechanism of disintegration involves, in large part, moisture absorption and swelling by an insoluble material. Examples of disintegrants include croscarmellose sodium and crospovidone which are typically incorporated into implants in the range of 1–20% of total implant weight. In many cases, soluble fillers such as sugars (mannitol and lactose) can also be added to facilitate disintegration of the implants.

Surfactants may be necessary in implant formulations to enhance wettability of poorly soluble or hydrophobic materials. Surfactants such as polysorbates or sodium lauryl sulfate are, if necessary, used in low concentrations, generally less than 5%.

Binders are adhesive materials that are incorporated in implant formulations to bind powders and maintain implant integrity. Binders may be added as dry powder or as solution. Sugars and natural and synthetic polymers may act as binders. Materials added specifically as binders are generally included in the range of about 0.5%–15% w/w of the implant formulation. Certain materials, such as microcrystalline cellulose, also used as a spheronization enhancer, also have additional binding properties.

Various coatings can be applied to modify the properties of the implants. Three types of coatings are seal, gloss and enteric. The seal coat prevents excess moisture uptake by the implants during the application of aqueous based enteric coatings. The gloss coat improves the handling of the finished product. Water-soluble materials such as hydroxypropyl cellulose can be used to seal coat and gloss coat implants. The seal coat and gloss coat are generally sprayed onto the implants until an increase in weight between about 0.5% and about 5%, preferably about 1% for seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as Eudragit•, RohmTech, Inc., Malden, Mass., and Aquateric•, FMC Corp., Philadelphia, Pa., can be used and are layered as thin membranes onto the implants from aqueous solution or suspension. The enteric coat is generally sprayed to a weight increase of about one to about 30%, preferably about 10 to about 15% and can contain coating adjuvants such as plasticizers, surfactants, separating agents that reduce the tackiness of the implants during coating, and coating permeability adjusters. Other types of coatings having various dissolution or erosion properties can be used to further modify implant behavior. Such coatings are readily known to one of ordinary skill in the art.

Preparation of Polymeric-Drug Compositions

Controlled release devices are typically prepared in one of several ways. For example, the polymer can be melted, mixed with the substance to be delivered, and then solidified by cooling. Such melt fabrication processes require polymers having a melting point that is below the temperature at which the substance to be delivered and polymer degrade or become reactive. Alternatively, the device can be prepared by solvent casting, where the polymer is dissolved in a solvent, and the substance to be delivered dissolved or dispersed in the polymer solution. The solvent is then evaporated, leaving the substance in the polymeric matrix. Solvent casting requires that the polymer be soluble in organic solvents and that the drug to be encapsulated be soluble or dispersible in the solvent. Similar devices can be made by phase separation or emulsification or even spray drying techniques. In still other methods, a powder of the polymer is mixed with the drug and then compressed to form an implant.

Methods of producing implants also include granulation, extrusion, and spheronization. A dry powder blend is produced including the desired excipients and microspheres. The dry powder is granulated with water or other non-solvents for microspheres such as oils and passed through an extruder forming "strings" or "fibers" of wet massed material as it passes through the extruder screen. The extrudate strings are placed in a spheronizer which forms spherical particles by breakage of the strings and repeated contact between the particles, the spheronizer walls and the rotating spheronizer base plate. The implants are dried and screened to remove aggregates and fines.

These methods can be used to make micro-implants (microparticles, microspheres, and microcapsules encapsulating drug to be released), slabs or sheets, films, tubes, and other structures. A preferred form for infusion or injection is micro-implants.

Administration to Patients

The chemotherapeutic agents described herein or their functionally equivalent derivatives can be administered alone or in combination with, either before, simultaneously, or subsequent to, treatment using other chemotherapeutic or radiation therapy or surgery. A preferred embodiment is the local administration, by implantation of a biocompatible polymeric matrix loaded with the chemotherapeutic agent, or injection/infusion of micro-implants, using dosages determined as described herein. The dosages for functionally equivalent derivatives can be extrapolated from the in vitro and in vivo data.

The composition can also be administered locally using an infusion pump, for example, of the type used for delivering insulin or other chemotherapeutic agents to specific organs or tumors, although the polymeric devices has clear advantages to the use of a pump, even an implanted pump having a refillable reservoir, particularly in view of the effective dosage ranges, which are so significantly less than those for systemic administration.

In the preferred method of administration, the polymeric implants are implanted at the site of a tumor, either following surgical removal or resection or by injection using microparticles less than about 100 to 200 microns in diameter injected by means of a catheter or syringe. If biodegradable polymers are used, it is not necessary to remove the implant following release of the chemotherapeutic.

The polymeric implants can also be combined with other therapeutic modalities, including radiotherapy, other chemotherapeutic agents administered systemically or locally, and immunotherapy.

The present invention will be further understood by reference to the following non-limiting examples.

EXAMPLE 1: In vitro efficacy of paclitaxel.

Cell culture. Tumor sensitivity to paclitaxel was measured by the clonogenic assay described by Rosenblum, et al., *Cancer* 41:2305–2314 (1978) and Salcman, et al., *Neurosurgery* 29:526–531 (1991) with rat glioma (9L, F98), human glioma (H80, U87, U373), and human medulloblastoma (D324) cell lines. Cells were grown and propagated in minimum essential medium (MEM) supplemented with 10% fetal bovine serum, L-glutamine, penicillin, and streptomycin and incubated at 37° C. in an atmosphere containing 5% $CO_2$. At the start of each assay, 600 tumor cells in 2 ml of medium were plated on Falcon 6-well tissue-culture plates (Becton-Dickenson, Lincoln Park, N.J.). After incubating for 24 h, the medium was removed from the places and replaced with 2 ml of medium containing paclitaxel and 0.1% dimethylsulfoxide (DMSO). The treatment solutions were prepared as described by Roytta et al., *Prostate* 11:95–106 (1987). The paclitaxel treatment solution was then either replaced with fresh paclitaxel-free media containing 0.1% DMSO after 1 or 24 h or was left on the places for the 6-to 8-day incubation period. At the end of the incubation period the plates were stained with a solution containing 0.63 g of Coomassie blue (Sigma), 125 ml of methanol, 87 ml of $H_2O$, and 38 ml of ascetic acid. The colonies on each plate were counted and the result was expressed as a percentage of the colonies formed on control plates not exposed to paclitaxel. Plating efficiencies for control plates ranged from 20% to 25%. A range of drug concentrations was applied to each set of cells. The percentage of cell kill values for the paclitaxel treatments were plotted as a function of the drug concentration used. The concentration of drug necessary to produce 1 log of cell kill ($LD_{90}$) was interpolated from the graph. Graphs were prepared and analyzed using Cricket Graph v. 1.3.2 (Cricket Software, Malvern, Pa.). Each determination was done in triplicate.

Chemicals. Paclitaxel for these experiments, which was provided by the NCI (NSC 125973/44), was used without further purification and stored as a bulk solid at 4° C. A 1 mM stock solution of paclitaxel in DMSO was prepared and kept at −20° C. until thawed for use. F98 glioma cells carried for five years were initially provided by Dr. Joseph Goodman, Department of Neurosurgery, Ohio State University, Columbus, Ohio. 91 glioma cells carried for eight years were originally obtained from Dr. Marvin Barker of the University of California, San Francisco, Calif. D324 (DAOY), described by Jacobsen, et al., *J. Neuropathol. Exp. Neurol.* 44:472–485 (1985) was provided by Dr. Henry Friedman, Division of Pediatric Hematology and Oncology, Department of Pediatrics, Duke University, Durham, North Carolina. U373, U87 (described by Beckman, et al., *Hum. Hered.* 21:238–241 (1971), and H80 (U251) (Bullard, et al., *J. Neuropathol. Exp. Neurol.* 40:410–427 (1981)) were obtained from the American Type Culture Collection, Rockville, Md.

Results

The effects of paclitaxel on colony formation in vitro in the rat glioma (9Lm F98), human glioma (U87, U373, H80), and human medulloblastoma (D324) tumor lines are shown in Table 3. All of the cell lines were sensitive to the drug when exposed continuously to paclitaxel for 6–8 days. Log cell kill ($LD_{90}$) occurred at values ranging between 3.9 (D324) and 4 nM (9L). The human tumor lines were uniformly more susceptible to paclitaxel than were the rat lines. Log cell kill occurred at nanomolecular paclitaxel concentrations for three (U87, U373, H80) of the four human lines studied, whereas four to ten times these amounts were required for the rat lines (9L, F98).

TABLE 3

LD$_{90}$ values for paclitaxel against malignant brain tumor cell lines as determined by clonogenic assay.

| Treatment duration | LD$_{90}$ concentration (nM) for | | | | | |
|---|---|---|---|---|---|---|
| | 9L | F98 | U373 | H80 | U87 | D324 |
| 1 h | 890 | | 280 | | | |
| 24 h | 100 | | 29 | | | |
| 6–8 days | 42 | 25 | 7.2 | 19 | 9.1 | 3.9 |

The duration of exposure to the drug significantly affected paclitaxel's potency in vitro. After exposure of cells to paclitaxel for only 1 h, the LD$_{90}$ increased by factors of more than 20 for the 9L line and 40 for the U373 lines as compared with the values recorded for the continuous (6- to 8-day) exposure. Cells exposed to paclitaxel for 24 h gave LD$_{90}$ values between those obtained for 1-h and continuous exposure. For example, for the human U373 line, FIG. 1 shows that the LD$_{90}$ for 1-h exposure was 280 nM, that for 24-h exposure was 29 nM, and that for continuous exposure was 7.2 nM for the human U373 line.

Paclitaxel has previously been shown to be stable in cell-culture medium, by Ringel, et al., *J. Pharmacol. Exp. Ther.* 242:692–698 (1987). It equilibrates with its equipotent epimer, 7-epitaxol, but undergoes significant (less than 10%) hydrolysis to inactive compounds. The potency of the paclitaxel solutions should therefore not have diminished during the course of the 6- to 8-day incubation.

These results demonstrate that paclitaxel is highly potent in vitro against the rat and human brain-tumor cell lines examined. Log cell kill occurred at nanomolecular concentrations of the drug, which is consistent with the reports of paclitaxel's activities against other malignancies in vitro. For example, nanomolecular concentrations of paclitaxel have been found to be cytotoxic in vitro against ovarian, breast, lung, and prostatic cancer and melanoma, as reported by Hanauske, et al., *Anticancer Drugs* 3:121–124 (1992); Rowinsky, et al., *Cancer Res.* 4093–4100 (1988); Roytta, et al., *Prostate* 11:95–106 (1987). Furthermore, paclitaxel has demonstrated efficacy against each of these tumors in clinical trials, as reported by Roth, et al., *Pr. Annu. Meet. Am. Soc. Clin. Oncol.* 11:A598 (1992); Rowinsky, et al., (1990). Brain tumors therefore appear to be as sensitive to paclitaxel in vitro as other tumor lines that are currently being treated with paclitaxel in clinical trials. Moreover, cell sensitivity to paclitaxel concentration increased significantly with increasing duration of exposure to the drug (from 1 h to 1 week) in vitro. This finding is consistent with previous investigators' reports on paclitaxel's action in vitro against other malignancies. Paclitaxel arrests the cell cycle during the late G$_2$ or M phase but does not slow cell progression through the preceding stages of cell replication, as described by Horwitz, et al., *Ann. NY Acad. Sci.* 466:733–744 (1986). Increasing the duration of exposure to paclitaxel allows more cells in a given sample to enter the cell-cycle phases during which paclitaxel is active. With shorter periods of exposure to the drug, a greater proportion of cells exist entirely outside the paclitaxel-sensitive G$_2$ and M phases during the treatment interval.

To maximize the clinical efficacy of paclitaxel, therefore, a drug delivery protocol that could maintain an elevated concentration of drug for an extended period would be desirable. To date, the protocols developed in clinical phase I trials have generally involved a single 1- to 24-h infusion repeated every 2-3 weeks or a 1- to 6-h infusion given once a day for 5 days. The elimination half-lives determined in these studies indicate that paclitaxel is cleared relatively rapidly with an elimination half-life, t½β, of between 1.3 and 8.6 h (Rowinsky, et al., (1988)). Since 93.5% of a drug is eliminated after four half-lives, most of the paclitaxel is dissipated in these regimens at between 5 and 26 h after its administration. The results described herein indicate, however, that paclitaxel's potency increases in vitro by a factor of two to four times when cells are exposed to paclitaxel for more than 24 h.

EXAMPLE 2: Preparation of paclitaxel implant.

Solid paclitaxel, obtained from Napro Biotherapeutics (Boulder, Co.) or from the National Cancer Institute (Bethesda, Md.), was mixed with poly[bis(p-carboxyphenoxy)propane-sebacic acid] copolymer (PCPP-SA) (20:80) synthesized according to the method of Domb, A. J., and R. Langer (*J. Polym. Sci.* 25:3373–3386 (1987)), the teachings of which are incorporated herein by reference, to give a mixture containing 0, 20, 30, or 40% paclitaxel by weight. The paclitaxel-polymer mixture was dissolved in methylene chloride (Fluka, Switzerland) to give a 10% solution (w:v). The solvent was evaporated with a nitrogen stream to yield a dry powder. Paclitaxel-polymer discs (10 mg final weight) were prepared by compression molding 11 mg of the paclitaxel-polymer powder with a stainless steel mold (internal diameter, 2.5 mm) under light pressure from a Carver Press at 200 psi. The discs were sterilized under UV light for 45 minutes.

EXAMPLE 3: Demonstration of paclitaxel delivery from a biodegradable matrix into the surrounding medium in vitro.

The efficiency of the delivery of paclitaxel incorporated into a biodegradable polymer into the surrounding medium was assessed in vitro as follows.

Preparation of polymer discs. Polymer discs were prepared as described above except that 3H-labeled paclitaxel (Atomic Energy Commission, Nuclear Research Center, Beer Sheva, Israel) was used in the polymer preparation. The 3H-labeled paclitaxel had a final specific activity of 0.019 μCi/mg and was obtained by mixing $^3$H-labeled paclitaxel at 6.2 Ci/mmol with 100 mg of unlabeled paclitaxel (Napro Biotherapeutics, Boulder, Co.; or National Cancer Institute, Bethesda, Md.) in methanol and then evaporating the solvent.

Protocol. The paclitaxel-loaded polymer discs were placed in a microporous polyethylene specimen capsule (8×8 mm internal diameter and height), which was immersed in 7 ml of 0.1M phosphate buffer, pH 7.4. The apparatus was placed in a 37° C. incubator. The releasing medium was replaced at specified times during the 45-day (1000 hour) incubation period, and the recovered solutions were analyzed by scintillation counting and high pressure liquid chromatography (HPLC). HPLC analysis to confirm the release of intact paclitaxel was performed by extracting 2 ml of solution with methylene chloride and evaporating to dryness. The product was then redissolved in methanol and injected onto a C$_{18}$ HPLC column (Licosphere-100RP-18, 5 mm; E Merck, Darmstadt, Germany) as part of a Merck Hitachi system composed of a L-4200 UV-Vis Detector, L-6200 intelligent pump, and D-2500 Chromato integrator). The mobile phase consisted of methanol:water (70:30) and detection was at 230 nm. Control solutions containing 100 mM paclitaxel in methanol were used to determine the retention time of paclitaxel under these conditions (6.73 to 9.04 minutes). Radioactive analysis to quantify the amount of paclitaxel release was done by mixing 200 μl of the releasing buffer solution with 4 ml of a scintillation mixture composed of toluene and Lumax (Landgraat, The Netherlands) scintillation mixture in a 2:1 volume ratio. This solution was counted on a 1211 Rack β-liquid scintillation counter (LKB-Wallac OY, Finland). Each measurement represents the average of 3 independent countings. At the end of the release period, the amount of drug remaining in the disc was quantified by dissolving the polymer remnant in methylene chloride and counting the solution by the above technique. Release was measured over time from discs containing 20, 30, and 40% paclitaxel by weight.

Figure 2:
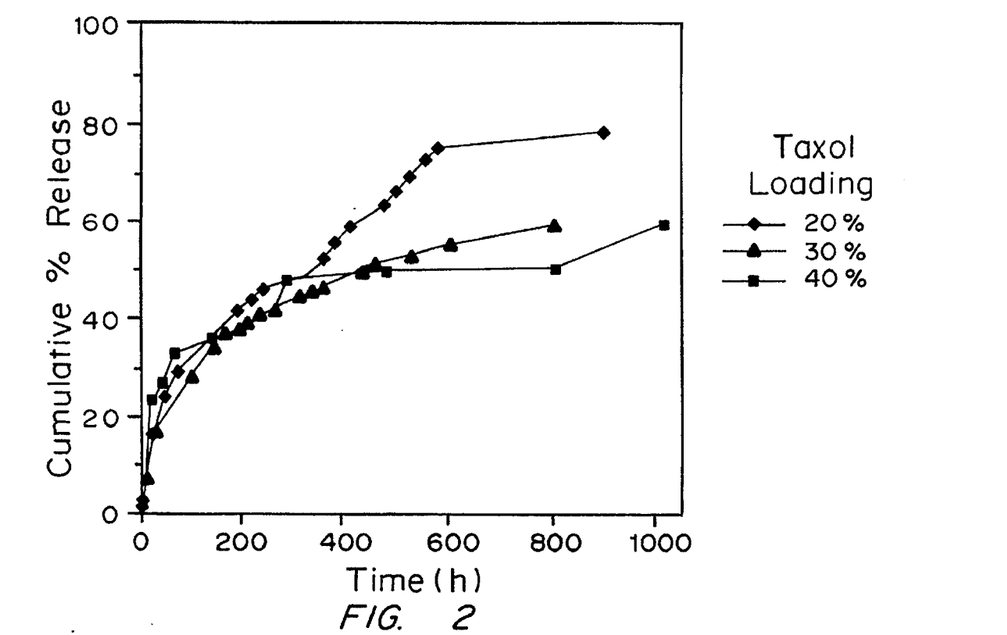
FIG. 2 is a graph of the cumulative percent release over time (hours) for PCPP-SA (20:80) polymer discs (10 mg) loaded with 20% (diamond), 30 (triangle) or 40% (square) by weight paclitaxel.

Results. The results of the in vitro drug release study are shown in FIG. 2, which illustrates that the delivery of paclitaxel from the biodegradable matrix into the surrounding physiological medium was efficient. HPLC confirmed that the paclitaxel released into buffer corresponded with intact paclitaxel. For each of the polymer loadings, a burst of drug release over the first few hours in solution was followed by essentially zero order kinetic release to the end of the experiment. The most efficient release was obtained from the 20% loaded disc, which released 80% of its loaded paclitaxel within the 1000 hour experimental period. The total amount of paclitaxel released from each disc was approximately the same, however: 1.6 mg for 20% disc, 1.8 mg for 30% disc, and 2.0 mg for 40% disc.

These results show that paclitaxel is released biphasically from the polymer, with an initial burst phase followed by a slower constant release phase. It is likely that the burst phase corresponds to the rapid release of paclitaxel particles embedded within the matrix surface, while the prolonged release represents slower release of paclitaxel from the center of the matrix.

The loading of the polymer does not seem to correlate directly with the amount of paclitaxel released during the experimental period. Although the 40% loaded polymer contained twice as much paclitaxel as the 20% loaded disc, the 40% loaded disc only released 1.25 times as much paclitaxel as the 20% loaded disc after 800 hours in a saline bath. If polymer degradation were the sole determining factor of paclitaxel release, then one would expect the loading to correlate directly with total drug released. Since the correlation appears weakened, another factor must be at least partially controlling paclitaxel release from the disc. Most likely, the low aqueous solubility of paclitaxel limits its uptake into media, despite breakdown of the matrix. Alternatively, the hydrophobicity of paclitaxel may inhibit hydrolysis of the polyanhydride matrix. While such interactions do not preclude the clinical use of this formulation, they do make the pharmacokinetics of the preparation more complex and the results less predictable when implanted in vivo as compared with topically applied or systemically administered.

EXAMPLE 4: Demonstration of Intracerebral Paclitaxel Delivery from the Polymer Matrix in Vivo The efficiency of the delivery of paclitaxel from the polymer matrix into surrounding brain tissue and the concentration of active paclitaxel within the brain, as measured up to one month after surgical implant, were assessed as follows.

Animals. Male Fischer 344 rats weighing 200–225 g were obtained from Harlan Sprague-Dawley, Inc. (Indianapolis, Ind.), kept in standard animal facilities with 4 rats/cage, and given free access to Certified Rodent Chow No. 5002 (Ralston Purina Co., St. Louis, Mo.) and to Baltimore city water.

Anesthesia. Rats were anesthetized with an intraperitoneal injection of 2–4 ml/kg of a stock solution containing ketamine hydrochloride (25 mg/ml), xylazine (2.5 mg/ml), and 14.25% ethyl alcohol in normal saline. They were allowed to recover in their cages following all surgical procedures.

Euthanasia. Prior to euthanasia, the rats were anesthetized as above. Euthanasia was accomplished with an intracardiac injection of 0.3 ml of Euthanasia-6 Solution CII™ (Veterinary Laboratories, Inc., Lenexa, Ks.).

Preparation of the paclitaxel loaded polymer. Polymer discs containing labeled paclitaxel were prepared as above, except that a small amount of 3H-labeled paclitaxel (specific activity, 19.3 Ci/mmol; National Cancer Institute) in toluene was added to the initial solution of polymer and paclitaxel in methylene chloride. The polymer-paclitaxel mixture was then dried in a vacuum desiccator and pressed into discs using a table vise calibrated to form a pellet.

Paclitaxel-polymer implantation. The procedure for polymer implantation in the rat has been described by Tamargo, R. J., et al. (*Cancer Res.* 53:329–333 (1993)), the teachings of which are incorporated herein by reference. Briefly, the heads of anesthetized rats were shaved and prepared aseptically. The skull was exposed with a midline incision, and a 3-mm burr hole was drilled through the skull 5 mm posterior and 3 mm lateral to the bregma. The dura was incised with a microsurgical knife (Edward Weck and Co., Inc., Research Triangle Park, N.C.), and the polymer disc was inserted into the brain parenchyma. The wound was irrigated and closed with surgical clips (Clay Adams, Parsippany, N.J.).

Protocol for intracerebral drug distribution. Twelve rats were given implants of 10-mg discs containing 40% paclitaxel by weight and 0.60 μCi/mg disc weight. At 3, 9, 17, and 30 days postimplantation, groups of 3 rats each were euthanized. The skull was opened and the brain exposed. The polymer disc was removed from the brain in situ. The brain was then removed from the skull and snap frozen in heptane over dry ice. The brain was sectioned in the midline into implant and contralateral hemispheres. Each hemisphere was sectioned coronally at 2-mm intervals by using a tissue blade grid consisting of individual tissue blades arranged in parallel separated by 2-mm metal spacers. Each section was weighed, dissolved in 15 ml Solvable homogenizing solution (New England Nuclear Dupont, Boston, Mass.), and combined with 15 ml Atomlight™ scintillation mixture (New England Nuclear Dupont). The brain samples were counted on a Beckman liquid scintillation counter. Raw counts were corrected for quenching and converted to dpm using a linear regression based on a series of quenched standards.

To convert dpm/mg tissue to paclitaxel concentration, a second experiment was performed. Four rats were given implants of 40% loaded polymer discs with 0.39 μCi/mg. One rat each was sacrificed at 3, 9, 17, and 30 days. The brain was removed and frozen as above. A 2-mm coronal section was taken through the site of the polymer implant. The section was minced and extracted with ethanol. The ethanol fraction was divided in two. The first half was dried in a vacuum desiccator and then resuspended in 100 μl of ethanol. Samples of this solution were spotted on silica thin layer chromatography plates (Sigma, St. Louis, Mo.). A solution of nonradioactive paclitaxel in ethanol was also applied to the plates over the ethanol extract. The plate was developed with methylene chloride:methanol (95:5) and exposed in an iodine chamber. The R$_f$ value for the paclitaxel was determined and each lane cut into 4 sections: A, origin; B, origin to paclitaxel spot; C, paclitaxel spot; and D, paclitaxel spot to solvent front. The chromatography strips were combined with Atomlight™ mixture and counted in a liquid scintillation counter. The distribution of labeled paclitaxel across the chromatography plate allowed determination of signal corresponding to intact drug. To determine the efficiency of extraction, the remaining half of the original extract was combined with mixture and counted, and the residual brain tissue was homogenized and counted as above. The paclitaxel concentration in ng/mg brain tissue was calculated by multiplying the percentage of intact paclitaxel by the dpm/mg brain and dividing by the specific activity of paclitaxel present in the polymer disc.

Results. The results of the intracerebral distribution studies, demonstrating that the implant is capable of producing elevated brain levels of paclitaxel throughout the rat brain. These results indicate that paclitaxel penetrates the brain parenchyma at concentrations that are theoretically tumoricidal in vitro and that paclitaxel concentration remains elevated intracranially for prolonged duration, extending the therapeutic period.

Paclitaxel from the implant was distributed widely throughout the rat brain. Concentrations were 100 to 1000 ng/mg brain tissue within 2 to 3 mm of the implant, but only 1 to 10 ng/mg in brain tissue more than 4 mm away from the implant and throughout the contralateral hemisphere. Paclitaxel concentrations increased slightly during the 30 days, correlating with additional drug released from the polymer disc. The percentage of radioactivity in each slice corresponding to intact paclitaxel as measured by thin layer chromatography did not change appreciably over the course of the experiment. At each time point, approximately 56±3% (standard error of the mean) of the raw counts represented parent drug. Thirteen±2% represented polar metabolites, and 31±3% were tissue bound. The detection limit for the overall assay was 0.2 ng/mg brain tissue.

Although paclitaxel concentration fell off sharply from 100 to 1000 ng/mg (µM) brain tissue in the implant hemisphere within 1 to 3 mm of the implant to 1 to 10 ng/mg (µM) brain tissue at the periphery of the rat brain (7 mm) and throughout the contralateral hemisphere, even these lower concentrations were 2 to 3 orders of magnitude higher than the 90% lethal dose concentrations of paclitaxel for several human (U87, U373, H80, D324) and rat (9L, F98) glioma lines in vitro. Given the hydrophobicity of paclitaxel, it is believed that these levels represent the saturation point of paclitaxel within the interstitial milieu.

Notably, paclitaxel concentration remained elevated for at least one month after implantation in the rat brain. Based on in vitro data, prolonging exposure to paclitaxel significantly decreases the concentration of paclitaxel necessary to achieve log cell kill for both glial and other tumors (Rowinsky, E. K., et al., *Cancer Res.* 48:4093–4100 (1988)). Thus, the polymer implant appears to maximize the antitumor benefit of paclitaxel. Pharmacokinetic studies from Phase I trials indicate that paclitaxel is cleared relatively quickly from the circulation with a β-half-life between 1.3 and 8.6 hours (Rowinsky, E. K., et al., *J. Matl. Cancer Inst.* 82:1247–1259 (1990)). Since 93.5% of a drug is cleared after four half-lives, it is unlikely that systemic administration could maintain such high intracranial paclitaxel concentrations for prolonged periods, especially since the blood-brain barrier limits uptake of the drug.

In comparison, studies examining the intracerebral distribution of the nitrosourea, BCNU, delivered from the PCPP-SA (20:80) polymer in the rabbit brain demonstrated that BCNU was initially distributed widely from the polymer, up to 12 mm from the implant site, with an average concentration of 8 mM (Grossman, S., et al., *J. Neurosurg.* 76:640–647 (1992)). Preliminary studies have shown that this concentration is two orders of magnitude higher than the 90% lethal dose for BCNU against rat glioma cells based on in vitro measurements. The amount of brain exposed to BCNU begins to decrease after three days. However, BCNU is only detectable within a 40 mm radius from the implant on Day 7 and only within a 3-mm radium by 21 days after implantation. In contrast and surprisingly, paclitaxel concentration is still constant or rising throughout the rat brain 30 days after implant. Thus, paclitaxel appears to be a better candidate than BCNU for sustained interstitial chemotherapy on a pharmacokinetic basis.

EXAMPLE 5: Demonstration of Amount of Implant Toxicity

The amount of toxicity associated with the paclitaxel loaded polymer implant in the brain was determined as follows.

Protocol. Animals were obtained, housed, anesthetized, and sacrificed as described above. PCPP-SA (20:80) discs (10 mg) containing 20, 30, and 40% paclitaxel by weight were implanted intracranially in rats by the technique described above. A group of control rats were given implants of blank PCPP-SA discs containing no paclitaxel. Rats were examined twice daily for signs of neurotoxicity with respect to grooming, response to startle stimulus, and gait. After 60 days, all surviving rats were sacrificed and their brains were removed and fixed in formalin. One coronal brain section centered through the polymer implant was taken for each rat and stained with hematoxylin and eosin.

Results. The results of the implant toxicity studies are shown in Table 4.

TABLE 4

Toxicity of Intracranial paclitaxel implants in Fischer 344 rats.

| Treatment | No. of Survivors/ total | Toxicity | Date of death (days postimplant) |
|---|---|---|---|
| Control PCPP-SA | 4/4 | —* | — |
| 20% paclitaxel | 1/4 | Ataxia, hemiparesis, weight loss, death | 41,53,53 |
| 30% paclitaxel | 4/4 | — | |
| 40% paclitaxel | 4/4 | — | |

*no observed clinical toxicity or death.

As shown in Table 4, there was no apparent acute clinical toxicity from the implant. All of the rats recovered from the implant surgery and were indistinguishable from controls in terms of motor activity, response to stimulus, and grooming. Two rats later developed ataxia and, subsequently, hemiplegia contralateral to the implant, weight loss, and death. One rat died spontaneously without a prodrome. All of the other rats remained neurologically intact throughout the experiment. Histological examination of brain tissue sections through the paclitaxel-polymer implant site showed scattered foci of karyorrhectic nuclei interspersed with areas of normal brain. In addition, there were scattered cytologically atypical cells with large, hyperchromatic, sometimes bilobed, nuclei. These atypical cells were more numerous around the implant site, but were seen bilaterally. The changes were present to varying degrees in the brains of all rats receiving the paclitaxel-polymer implant, but were absent in rats receiving the blank PCPP-SA disc, indicating that the cytological changes were a result of the paclitaxel exposure. There was no quantitative or qualitative difference in the visible cytological changes occurring in animals with paclitaxel implants either between groups with different paclitaxel concentration implants or between animals that exhibited gross neurobehavioral toxicity and those that did not. The degree of cytological pathology was, therefore, spread evenly among the different paclitaxel-polymer preparations.

A minimal amount of clinical and histological toxicity was associated with the paclitaxel-polymer implant in the rat brain. Three of the 12 rats receiving the implant (20% loaded polymer) without tumor died during the 60-day experimental period, while the other rats tolerated the treatment without any apparent clinical symptoms. Two rats receiving paclitaxel (20 and 30% loaded polymers) after tumor implantation also died without visible tumor, but with the atypia found in all the rats receiving the paclitaxel implant. These atypical changes were consistent with similar cytological alterations produced by a wide variety of chemotherapeutic agents. The symptoms of overt toxicity appeared late in the experiment, 30 days or more after implant, indicating that acute toxicity is not a primary concern. Interestingly, all the rats receiving the paclitaxel implant had cytological abnormalities visible on microscopic examination, and there was no correlation between the degree of atypia and the presence or severity of clinical toxicity. From the pharmacokinetic measurements of intracerebral drug distribution following implantation, it is apparent that these devices produced high drug concentrations distributed throughout the rat brain. These concentrations were maintained intracranially, for at least one month after implant. It is not surprising, therefore, that the brain itself was affected after prolonged exposure to such high paclitaxel concentrations. Nevertheless, several rats from the tumor-polymer studies lived 120 days or more after implantation, and two lived for one year.

Lower doses of paclitaxel could be used in patients, either from a proportionately smaller polymer disc or from a disc with a lower percentage loading of paclitaxel. These doses could be better tolerated for chronic therapy clinically. Other agents administered interstitially to the brain have been reported to show toxicity in animal models without measurable toxicity in clinical trials. Appropriate dosages for treatment of patients can be determined using standard and routine methods.

EXAMPLE 6: Demonstration of the Efficacy of the Paclitaxel Loaded Polymer Implant at Extending Survival in Rats Bearing Intracranial 9L Gliosarcoma.

The efficacy of the paclitaxel loaded polymer implant at extending survival in rats bearing intracranial 9L gliosarcoma was measured as follows.

Tumor. The 9L gliosarcoma was obtained in 1985 from Marvin Barker, Brain Tumor Research Center, University of California, San Francisco, Calif., and maintained subcutaneously in the flank of male Fischer 344 rats. The tumor was passaged every 2 to 3 weeks. To harvest tumor for passage and intracranial studies, the flank of a rat bearing the 9L gliosarcoma was shaved and prepared aseptically with 70% ethanol and povidone-iodine. An incision was made in the flank, and the tumor was removed en bloc and sectioned into 1-mm$^3$ pieces, which were kept in saline over ice during the implantation surgery (4 hours).

Protocol for the intracranial efficacy study. Two separate experiments examining the efficacy of the paclitaxel-polymer implant against the intracranial 9L glioma were performed. Based on in vitro clonogenic assays, the 9L glioma appears relatively resistant to paclitaxel compared to human glioma cells. Intracranial tumor implantation in the rat was performed according to the technique described by Tamargo et al. (1993), the teachings of which are incorporated herein. Briefly, a burr hole was drilled in the dura incised as described above. The cortex and white matter were resected with suction until the superior aspect of the brainstem was visualized. The wound was packed with sterile gauze for 10 minutes to control any bleeding. The gauze was then removed, and a 1-mm$^3$ piece of the 9L gliosarcoma was introduced into the cranial defect and placed on the brainstem. The wound was irrigated and closed with wound clips. Surgery to implant the polymer-chemotherapy device was performed five days later. The rats were randomized to one of the treatment or control groups and weighed. The original incision was reopened aseptically and the placement of the tumor was confirmed. A cruciate incision was made in the surface of the tumor and the polymer disc advanced into the tumor. Treatment rats received 10 mg PCPP-SA discs containing 20, 30, or 40% paclitaxel by weight, while control rats received blank 10 mg PCPP-SA discs containing no paclitaxel. Tamargo et al. have demonstrated that there is no survival difference between rats with intracranial 9L gliomas treated with the blank PCPP-SA discs and rats given a "sham" operation without any implant. Any bleeding was allowed to subside spontaneously, and the wound was irrigated with 0.9% saline and closed with surgical staples. The rats were examined twice daily and the time to death recorded. Long term survivors were sacrificed either 120 days (Experiment 1) or 1 year (Experiment 2) after implant. At death, the brain was removed and fixed in formalin. A coronal section was taken through the polymer implant site and stained with hematoxylin and eosin. The section was examined to confirm the presence or absence of tumor growth. Survival was plotted on a Kaplan-Meier survival curve and statistical significance was determined by a nonparametric Kruskal-Wallis analysis of variance followed by a nonparametric studentized Newman-Keuls test for multiple comparisons, as described by Zar, J. M., *Biostatistical Analysis*, Prentice-Hall, Inc., Englewood Cliffs, N.J. (1984), the teachings of which are incorporated herein by reference.

The results of the intracranial efficacy studies are shown in Table 5.

TABLE 5

Efficacy of intracranial paclitaxel implants versus rat 9L gliosarcoma.

| Experiment | Treatment | No. of rats | Median survival (days) | % increase life span | No. of long term survivors* | P value |
|---|---|---|---|---|---|---|
| 1 | Control | 8 | 19.5 | | 0 | |
| | 40% Taxol™ | 6 | 38.0 | 95 | 2 | <0.02 |
| | 30% Taxol™ | 8 | 45.0 | 131 | 1 | <0.002 |
| | 20% Taxol™ | 8 | 61.5 | 215 | 2 | <0.001 |
| 2 | Control | 7 | 18.0 | | 0 | |
| | 40% Taxol™ | 8 | 35.5 | 97 | 2 | <0.005 |
| | 30% Taxol™ | 8 | 27.0 | 50 | 0 | <0.05 |

*Long term survivors were alive at 120 days postimplant.
Results of nonparametric Newman-Keuls test comparing treatment groups to control.
The generic name for Taxol™ is paclitaxel.

As shown in Table 5, two separate experiments established that the paclitaxel polymer implant significantly extended survival in rats bearing the intracranial 9L gliosarcoma compared to control animals. Survival was extended from 1.5 to 3.2-fold (P values from <0.05 to <0.001, respectively, nonparametric Newman-Keuls test). Each polymer preparation produced several long term survivors (120 days or longer from tumor implant). The two long term survivors from Experiment 2 were allowed to live for 1 year prior to sacrifice. None of the surviving animals had visible tumor on autopsy either grossly or microscopically in hematoxylin and eosin-stained sections. In contrast, all animals in the control groups died with large intracranial tumors. There was no significant survival difference among the treatment doses of each experiment (P>0.05, nonparametric Newman-Keuls).

Figure 3:
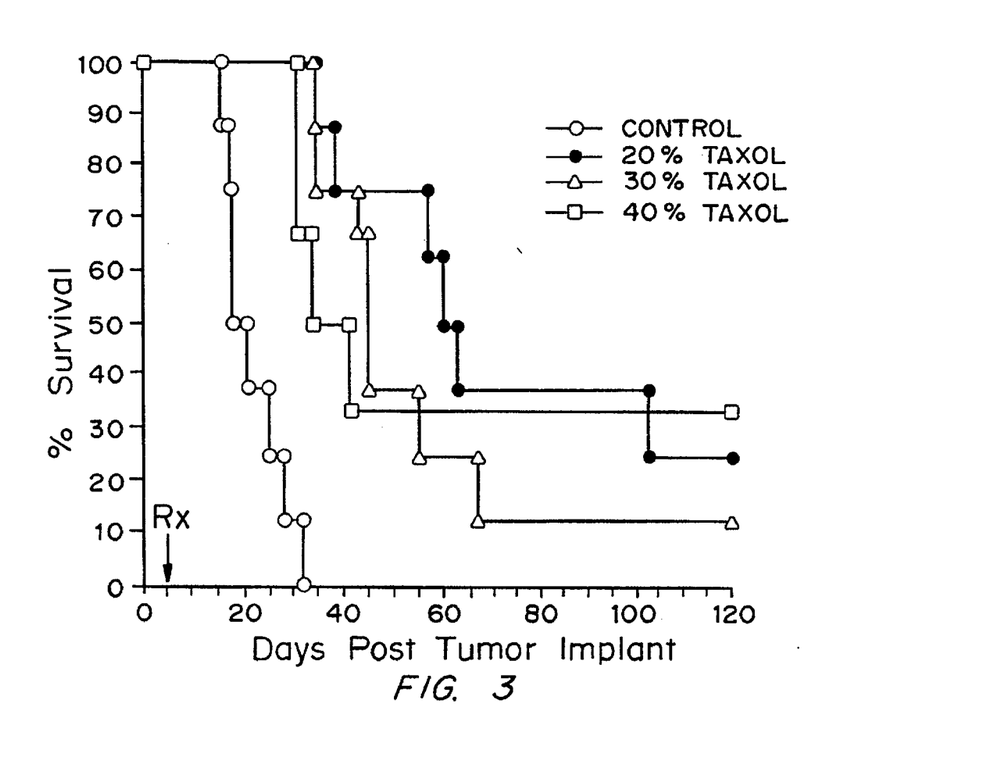
FIG. 3 is a graph of percent survival over time in days (Kaplan-Meier survival curves) in rats receiving an intracranial 9L gliosarcoma tumor implant on day 0 and were treated on day 5 with an intratumoral implant consisting of a 10-mg disc of PCPP-SA (20:80) loaded with 20, 30 or 40% paclitaxel by weight. Control animal received a 10 mg PCPP-SA (20:80) implant with no loaded drug.

In addition, two animals (20% and 30% loaded polymer groups) in Experiment 1 died during the experimental period without macro- or microscopic evidence of tumor growth. Scattered foci of atypical and karyorrhectic cells similar to those seen in the rats receiving the paclitaxel implant without tumor were present in these brains as well as in the brains of rats surviving to the end of the experimental period. The Kaplan-Meier curve for Experiment 1 is shown in FIG. 3.

Thus, the paclitaxel-polymer devices extended the median survival of rats bearing intracranial tumors 1.5- to 3.0-fold (P <0.05 to <0.001) compared to controls.

EXAMPLE 7: Demonstration of the Release Kinetics of Camptothecin from a Biocompatible Polymer Polymer preparation. EVAc (40% vinyl acetate by weight; Elvax 40P) was obtained from Dupont (Wilmington, Del.). The EVAc was washed in absolute ethyl alcohol to extract the inflammatory antioxidant butylhydroxytoluene, as described by Langer, R., et al., *J. Biomed. Mater. Res.* 15:267–277 (1981), the teachings of which are incorporated herein by reference. Sodium camptothecin, obtained from the National Cancer Institute, was incorporated into the polymer matrix by a modification of the procedure described by Rhine, W. D., et al., *J. Pharm. Sci.* 69:265–270 (1980), the teachings of which are incorporated herein by reference. Camptothecin and EVAc were combined to yield 20%, 40%, or 50% loaded polymers by weight. Methylene chloride was added to the mixture to yield a 10% solution of EVAc and methylene chloride and agitated on a Vortex mixer until completely dissolved. The solution of camptothecin-EVAc-methylene chloride was then poured into a glass mold at −70° C. After 20 minutes, the solidified polymers were transferred to a −30° C. freezer for 4 days. The polymers were then placed in a vacuum desiccator for 4 days at room temperature to facilitate evaporation of methylene chloride, after which they were stored at 4° C.

Protocol. EVAc polymers loaded with camptothecin were placed in 3.0 ml of 0.9% NaCl in a 37° C. incubator. The solution was removed at various time points and replaced with fresh 0.9% NaCl, thus maintaining the concentration of camptothecin in the release medium at infinite sink conditions. The amount of camptothecin released into the solution was measured by HPLC, as described below. The cumulative dose released was determined by combining the release values at each time point.

HPLC method for measuring camptothecin. Quantitative analysis was performed on a Beckman chromatographic system equipped with a 507 Autosampler, 126AA solvent module, 166 Detector, and a System Gold data system. The column was a reverse-phase microbondpak C18 Waters column (particle size 10 µm, 3.9×300 mm), which was protected by an Uptight Precolumn (Upchurch Scientific, Inc.). The HPLC system was eluted isocratically with methanol:water (63:37; v/v) at room temperature. The flow rate of the mobile phase was 1.0 ml/minute, and samples were measured at a wavelength of 254 nm. A standard curve was constructed by plotting peak area against concentration.

Figure 4:
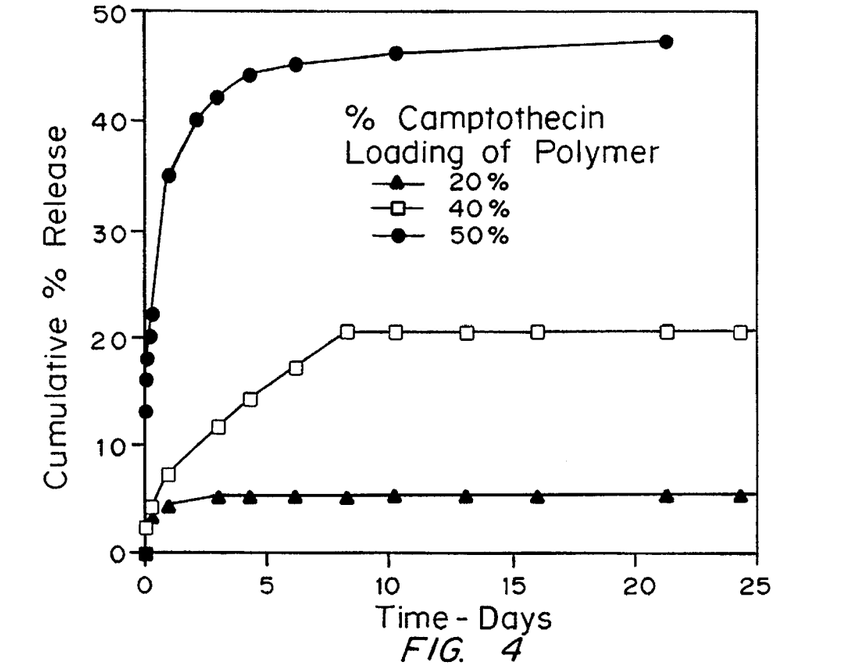
FIG. 4 is a graph of the in vitro cumulative percent release over time in days from 10 mg ethylene vinyl acetate (EVAc) polymer implants formulated with 20 (triangle), 40 (square), and 50 (circle) percent camptothecin by weight. Each point represents the mean of three measurements.

Results. EVAc polymers were prepared with loadings of 20%, 40%, and 50% camptothecin by weight. The average polymer weight was 10 mg. Thus, the total drug loads were approximately 2 mg, 4 mg, and 5 mg, respectively. The results of the release kinetic studies are shown in FIG. 4. With 50 percent loading, an initial burst of camptothecin was released from the polymer and steady state release was attained by 3 days, lasting at least 21 days. The 20% and 40% loadings yielded less camptothecin at each time point. The 50% loaded polymer was therefore selected for evaluation of efficacy in vivo based on these properties.

EXAMPLE 8: Demonstration of the Efficacy of Camptothecin in Treating Gliosarcoma Cells in Vitro Tumor cell lines. The 9L gliosarcoma cells were obtained in 1985 from Dr. Marvin Barker of the University of California, San Francisco, Calif. The F98 glioma cells were provided by Dr. Joseph Goodman, Department of Neurosurgery, Ohio State University, Columbus, Ohio. The human glioma cell lines U87 and U373 were provided by Dr.

O. Michael Colvin, Johns Hopkins University School of Medicine, Baltimore, Md. JH1 is a cell line established from a biopsy specimen from a patient with a pathologically confirmed glioblastoma multiform.

Cell culture of freshly biopsied gliomas. Biopsy samples were obtained from the operating room and transported in sterile specimen containers. Specimens were filtered through a 230 µm mesh cellector screen (Bellco Glass, Inc., Vineland, N.J.) with use of a glass pestle. The specimen was then centrifuged at 1000 rpm for 10 minutes. The supernatant fraction was discarded and the cell pellet was resuspended in 1 ml of minimum essential medium (Gibco BRL, Grand Island, N.Y.) with 10% fetal bovine serum, 0.5% L-glutamine, penicillin (base; 80.5 units/ml), and streptomycin (80.5 µg/ml). The suspension was passed through progressively smaller needles until it passed easily through a 25 gauge needle, after which it was recentrifuged at 1000 rpm for 5 minutes. The supernatant fraction was discarded and the pellet was resuspended in 5 ml of medium. This suspension was plated onto T75 culture flasks at various dilutions and incubated at 37° C. The medium was changed approximately every 3 days. When the initial culture reached confluence, the cells were trypsinized and passaged. Sensitivity was assessed by the clonogenic assay below, beginning with the second passage.

Clonogenic assay. The sensitivity of each glioma cell line was tested in a clonogenic assay. At confluence, the cells were trypsinized and plated at 400 cells per 60 mm well. After 24 hours, fresh medium containing camptothecin at various concentrations was added. For brief exposure experiments, the camptothecin was removed and replaced with fresh medium after 1 hour; for continuous exposure, medium was left in place for 7 days. At 7 days, all plates were fixed and stained with coomassie brilliant blue (Bio Rad, Richmond, Calif.). Colonies containing more than 50 cells were identified and counted. Treatments were performed in triplicate. Survival was calculated as the number of colonies formed by the treated cells relative to the number of colonies formed by the untreated cells.

Results. The results of the exposure of gliomas to camptothecin in cell culture are presented in Table 6.

TABLE 6

| In vitro sensitivity of gliomas to camptothecin | | |
|---|---|---|
| Cell Line[a] | LD90 1 Hour Exposure (µM) | LD90 Continuous Exposure (µM) |
| F98 | 1.40 | 0.10 |
| 9L | 1.40 | 0.10 |
| U87 | 1.20 | 0.10 |
| U373 | 0.30 | 0.026 |
| JH1 | 0.10 | 0.026 |

[a]F98 and 9L are rat glioma lines. U87 and U373 are established human glioma lines. JH1 is a glioblastoma line established at Johns Hopkins Hospital directly from a biopsy specimen. All were tested for sensitivity to camptothecin in a clonogenic assay.

The experiment was designed to assess the sensitivity of gliomas in vitro to a brief (one-hour) exposure and a continuous (seven-day) exposure. When exposed for 1 hour, the LD90 ranged from 1.4 µM for 9L, F98, and U87 to 0.3 µM for U373 cells. For all the cell lines, continuous exposure for 7 days decreased the LD90 by 10- to 100-fold. For the rat and established human cell lines, the LD90 after continuous exposure was approximately 0.1 µM or less. The human glioma line JH1 established directly from tumor obtained in the operating room showed the highest sensitivity to camptothecin at both exposure times. Total cell kill for JH1 was achieved at a concentration of 0.14 µM after a 1-hour exposure and 0.03 µM after continuous exposure.

EXAMPLE 9: Demonstration of the Efficacy of Camptothecin in Treating Gliosarcoma in Vivo Animals. Male Fischer 344 rats weighing 200–250 g were obtained from Harlan Sprague Dawley, Inc. (Indianapolis, Ind.). The animals were kept in standard animal facilities and given free access to Certified Rodent Chow No. 5002 (Ralston Purina Co., St. Louis, Mo.) and to Baltimore city water.

Gliosarcoma 9L Intracranial model. The 9L gliosarcoma was maintained in the flanks of male Fischer 344 rats. For intracranial implantation, the tumor was surgically excised from the carrier animal and cut into 1×2×2 mm pieces. The pieces were kept in sterile 0.9% NaCl on ice during the implantation procedure.

Male Fischer 344 rats were anesthetized with an intraperitoneal injection of 3–5 ml/kg of a stock solution containing ketamine hydrochloride 2.5 mg/ml, xylazine 2.5 mg/ml, and 14.25% ethyl alcohol in 0.9% NaCl. The surgical site was shaved and prepared with 70% ethyl alcohol and Prepodyne™ solution. After a midline incision, a 3 mm burr hole centered 5 mm posterior to the coronal suture and 3 mm lateral to the sagittal suture was made. The dura was opened and the cortex and white matter were resacted by using gentle suction until the brainstem was visualized. The surgical site was irrigated until clear with sterile 0.9% NaCl. A single tumor piece was placed in the depths of the cortical resection. The skin was closed with surgical staples.

Protocols for systemic and local delivery of camptothecin. Animals were divided into four treatment groups and received camptothecin either by intraperitoneal injection or polymer-mediated local delivery. Intraperitoneal injections of camptothecin were given on days 5, 6, 7, and 8 after tumor implantation at doses of 4, 10, 20, and 40 mg/kg/day. For local delivery by polymer, camptothecin was incorporated into EVAc at a dose of 50% by weight. Polymer cylinders measuring 1×3 mm were fashioned and placed under ultra violet light for sterilization for 1 to 2 hours prior to implantation. The polymers weighed on average 9.2 mg, and therefore each contained 4.6 mg of camptothecin. Polymers were placed directly into the tumor through the original burr hole 5 days after tumor implantation. Control animals and those receiving systemic camptothecin received blank intratumoral EVAc polymers of similar size and weight on day 5. Animals were assessed daily for signs of toxicity, especially neurological and behavioral changes. Deaths were quantified daily. At the time of death, the brain was removed and placed in 10% formalin for at least 1 week. The brains were prepared for hematoxylin and eosin staining. Sections through the tumor were stained to verify the presence of tumor.

Statistics. For the animal efficacy studies, survival was plotted on a Kaplan-Meier survival curve and statistical significance was determined by the Kruskal-Wallis nonparametric analysis of variance followed by the nonparametric analogue of the Newman-Keuls multiple comparison test.

Results. Camptothecin was evaluated for its potential to prolong survival in the rat 9L intracranial model when administered either systemically or by local polymer-mediated delivery. Table 7 shows the survival data for the different treatment groups.

TABLE 7

Efficacy of Camptothecin Against intracranial 9L Gliosarcoma in Fischer 344 rats

| Treatment group term | N | Method of drug delivery | Dose | Median Survival (Days) | Long Term survivors[a] | P value[b] |
|---|---|---|---|---|---|---|
| Control | 20 | * | Blank Intracranial EVAc | 19 | 0/20 | — |
| Systemic Campto 20 | 20 | i.p./* | Camptothecin 20 mg/kg/day × 4 days | 23 | 0/5 | NS[c] |
| Systemic Campto 40 | 5 | i.p./* | Camptothecin 40 mg/kg/day × 4 days | 11 | 0/5 | NS |
| Campto polymer | 17 | Intratumoral EVAc Polymer | 50% load Average polymer weight = 9.2 mg | >120 | 10/17 | <0.001 |

*Denotes treatment groups that received blank intratumoral discs of EVAc.
[a]Long term survivors lived greater than 120 days.
[b]Results of nonparametric Newman-Keuls test comparing treatment groups to control.
[c]NS, Not significant.

Figure 5:
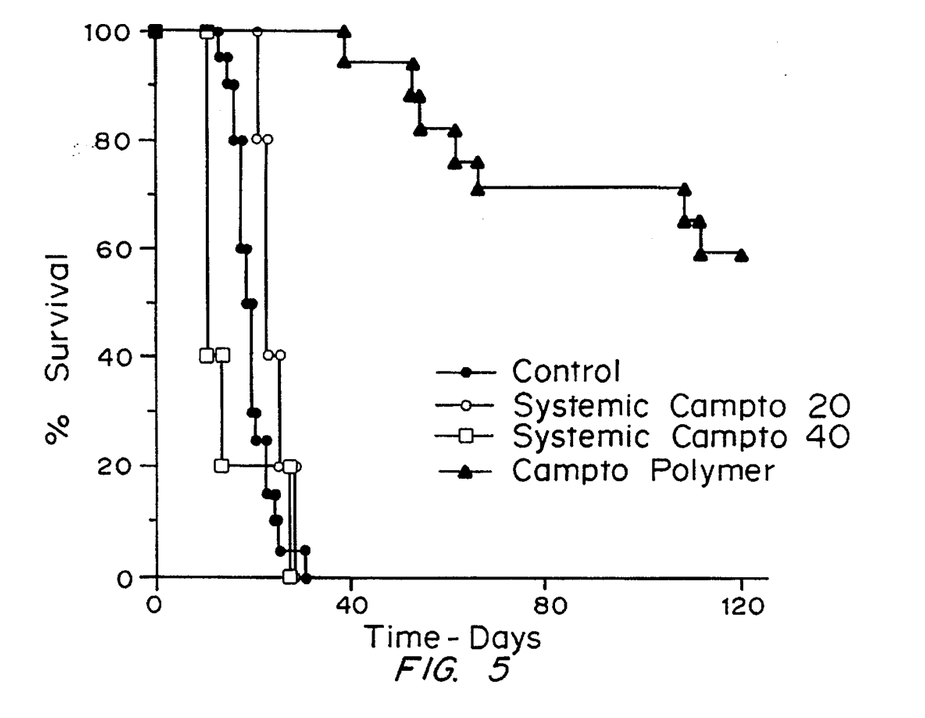
FIG. 5 is graph of percent survival over time in days (Kaplan-Meier survival curves) comparing systemic delivery of camptothecin with local delivery from EVAc polymers. Rats received an intracranial 9L gliosarcoma implant on day 0 and treatment was initiated on day 5. Control animals and those treated with i.p. camptothecin received a 9.0 mg EVAc polymer implant with no loaded drug. Systemic camptothecin at 20 or 40 mg/kg/day was administered i.p. over four days, beginning on day 5. The camptothecin polymer group received a 9.2 mg intratumoral implant of EVAc loaded with 50% camptothecin by weight.

Camptothecin, delivered by the polymer, significantly extended survival compared to controls, with 59% of the animals surviving long term (greater than 120 days, P <0.001). Systemic delivery of camptothecin did not increase survival relative to controls. Rather, at the highest dose tested, 40 mg/kg/day for 4 days, the animals died before the controls, although this result was not statistically significant. Kaplan-Meier survival curves are shown in FIG. 5. There were no signs of neurological or behavioral abnormalities noted in any of the animals.

These data show that camptothecin can be effectively utilized by local delivery with a controlled release polymer to prolong survival in rats implanted intracranially with 9L gliosarcoma. Further, the data show that local controlled drug delivery allow the clinical use of this highly effective drug that could not be utilized systemically because of its toxicity and narrow therapeutic window.

Modifications and variations of the compositions of the present invention and methods for use will be obvious to those skilled in the art from the foregoing detailed description. Such modifications and variations are intended to fall within the scope of the appended claims.

We claim:

1. A chemotherapeutic composition comprising
   a biocompatible polymeric matrix and a water insoluble, lipid insoluble chemotherapeutic agent, which does not cross the blood-brain barrier,
   wherein the agent is incorporated into and released from the polymeric matrix by degradation of the matrix or diffusion of the agent out of the matrix over a period of time of at least eight hours in an amount effective to inhibit growth of a solid tumor when administered to the tumor.

2. The composition of claim 1 wherein the chemotherapeutic agent is paclitaxel.

3. The composition of claim 1 wherein the chemotherapeutic agent is camptothecin.

4. The composition of claim 1 wherein the polymer matrix is biodegradable.

5. The composition of claim 4 wherein the polymeric matrix is formed of a polymer selected from the group consisting of polyanhydrides, polyhydroxy acids, polyphosphazenes, polyorthoesters, polyesters, polyamides, polysaccharides, polyproteins and copolymers and blends thereof.

6. The composition of claim 1 wherein the polymeric matrix is formed of ethylene vinyl acetate.

7. The composition of claim 1 further comprising additional biologically active compounds selected from the group consisting of chemotherapeutics, antibiotics, antivitals, antiinflammatories, cytokines, immunotoxins, anti-tumor antibodies, anti-angiogenic agents, anti-edema agents, radiosensitizers, and combinations thereof.

8. A method of administering to a patient in need of treatment a water insoluble, lipid insoluble chemotherapeutic agent comprising
   administering the chemotherapeutic agent locally adjacent or in a solid tumor,
   wherein the agent is incorporated into and released from a polymeric matrix by degradation of the polymer matrix or diffusion of the agent out of the matrix over a period of time of at least eight hours,
   wherein in an amount effective to inhibit growth of the solid tumor.

9. The method of claim 8 wherein the chemotherapeutic agent is paclitaxel.

10. The method of claim 8 wherein the chemotherapeutic agent is camptothecin.

11. The method of claim 8 wherein the chemotherapeutic agent is locally delivered by direct infusion to the tumor.

12. The method of claim 8 wherein the chemotherapeutic agent is locally delivered by implantation of the biocompatible polymer matrix incorporating the chemotherapeutic agent.

13. The method of claim 12 wherein the polymer matrix is biodegradable.

14. The method of claim 13 wherein the polymeric matrix is formed of a polymer selected from the group consisting of polyanhydrides, polyhydroxy acids, polyphosphazenes, polyorthoesters, polyesters, polyamides, polysaccharides, polyproteins, and copolymers and blends thereof.

15. The method of claim 12 wherein the polymeric matrix is formed of ethylene vinyl acetate.

16. The method of claim 8 further comprising administering radiation in combination with the composition.

17. The method of claim 8 further comprising administering with the chemotherapeutic agent additional biologically active compounds selected from the group consisting of chemotherapeutics, antibiotics, antivitals, antiinflammatories, cytokines, immunotoxins, anti-tumor antibodies, anti-angiogenic agents, anti-edema agents, radiosensitizers, and combinations thereof.

18. The method of claim 8 wherein the composition is in the form of micro-implants and are administered by injection or infusion.

* * * * *